United States Patent [19]

Mori

[11] Patent Number: 4,995,712

[45] Date of Patent: Feb. 26, 1991

[54] LIGHT RADIATION STAND

[76] Inventor: Kei Mori, 3-16-3-501, Kaminoge, Setagaya-ku, Tokyo, Japan

[21] Appl. No.: 429,872

[22] Filed: Oct. 30, 1989

[30] Foreign Application Priority Data

Mar. 28, 1989 [JP] Japan .................................. 1-35235

[51] Int. Cl.$^5$ ........................... G02B 5/08; G02B 7/18
[52] U.S. Cl. .................................... 350/603; 350/632; 350/639; 248/474; 248/476; 128/22; 128/395; 362/32; 362/139; 362/141; 362/142
[58] Field of Search ............... 350/603, 631, 632, 639; 248/469, 474, 476, 481; 128/21, 22, 395, 398; 362/32, 138, 139, 140, 141, 142

[56] References Cited

U.S. PATENT DOCUMENTS

| 90,746 | 6/1869 | Hartmann | 248/480 |
| 257,646 | 5/1882 | Beseler | 128/22 |
| 1,190,050 | 12/1915 | Verba | 350/639 |
| 4,843,530 | 6/1989 | Mori et al. | 362/32 |
| 4,844,069 | 7/1989 | Mori | 128/395 |

Primary Examiner—Bruce Y. Arnold
Assistant Examiner—R. D. Shafer
Attorney, Agent, or Firm—Jordan and Hamburg

[57] ABSTRACT (1) A light radiation stand for holding a fiber optic cable which transmits light rays therethrough and emits the same from its light-emitting end is described. The light radiation stand has a pole removably mounted to the stand and a mirror rotatably mounted on said pole. The mirror has a concave surface on one side and a convex surface on the other side. Furthermore a plane mirror is rotatably mounted on the middle portion of the pole.

1 Claim, 5 Drawing Sheets

LIGHT RADIATION STAND

BACKGROUND OF THE INVENTION

The present invention relates to a light radiation stand and more particularly to one by which light rays, transmitted through a light-guiding cable, can be radiated onto any desired part of a human body while making it possible to visually observe, by means of mirrors, where and how the irradiation is being carried out.

In recent years, a large number of persons suffer from strange new diseases, hard to cure diseases such as gout, neuralgia and rheumatism or pain from injury scars and bone fracture scars.

Furthermore, no one can be free from the skin's aging which progresses gradually from a comparatively young age. On the other hand, the present applicant has previously proposed focusing the sun's rays or artificial light rays by using lenses or the like to guide them into a fiber optic cable and to transmit them to any place where the light is needed for illumination or for other purposes as for example, to cultivate plants, chlorella, fish or the like. In the process of research, it has been found that visible light not containing ultraviolet and infrared rays is effective not only to promote the health of persons and prevent people's skin from aging by increasing the living body's activity but is also capable of noticeably helping in the healing of gout, neuralgia, rheumatism, bedsores, skin diseases, burn scars, bone fracture scars and so on and in relieving the pain from such diseases.

And furthermore, on the basis of the above-mentioned inventor's discovery, the applicant has previously proposed a light radiation device for use in medical treatment which can radiate visible light containing none of the harmful ultraviolet and infrared rays with the aim of using it for healing various kinds of diseases, for giving beauty treatments and for promoting health.

The present applicant has previously proposed a light radiation device for use in medical treatment. The device has a fiber optic cable for receiving sunlight or artificial light at its input end and for transmitting the same therethrough. The light to be transmitted through said fiber optic cable is one that corresponds to visible-spectrum light (white-colored light) obtainable in various ways as was previously proposed by the present applicant. Furthermore the device has a hood member installed at the light-emitting end portion of said fiber optic cable. At the time of giving medical treatment, a patient is placed in the chair and the visible-spectrum light thus transmitted through the fiber optic cable is radiated onto the diseased part of the patient.

As mentioned above, the light to be radiated onto the diseased part of the patient is the one that corresponds to the visible-spectrum components of the sunlight and is free from harmful elements such as ultraviolet and infrared rays. Consequently, it may be possible to give medical treatments safely without fear of exposing a patient to harmful ultraviolet and infrared rays. However, the above-mentioned light radiation device has some drawbacks such as it is too large and too expensive to be used in a family setting.

In view of the foregoing, the present applicant has previously proposed a light radiation stand which is suitable for home use for radiating the light transmitted through a fiber optic cable.

The light radiation stand previously proposed by present comprises applicant a stand base, one or more deformable flexible conduits vertically installed at the stand base, a holding means secured at the top of each conduit so as to removably hold the cable. The light-emitting end of the cable is usually supported by the holding means when light radiation is conducted. When the cable is used while being supported by the stand, its light-emitting end can easily be directed in any desired direction by bending the conduit since said conduit can be freely bent and kept in that state. When the stand is not used for a long period, it can be stored in any desired place with a small area since the cable can be removed from it.

As mentioned above, irradiating the skin's surface with light rays transmitted through a fiber optic cable can promote the health of persons and prevent people's skin from aging by increasing the body's life-sustaining activity.

Furthermore, it can aid in healing various kinds of diseases and scars and also aid in relieving the pain from such diseases. However, in the case of radiating the light rays, in particular, onto the face or other parts of the body that one cannot see oneself, one always feels anxious about the result of the radiation owing to the impossibility of checking how and where the light rays are falling. To solve this problem a hand mirror was adopted but it was found to be of no practical use and to be rather inconvenient because a patient could not hold a hand mirror for a long time and a suitable hand mirror was not always kept at hand.

SUMMARY OF THE INVENTION

It is an object of the present invention to provide a light radiation stand having a pole being removable together with mirrors integrally mounted thereon.

It is another object of the present invention to provide a light radiation stand having a mirror being rotatably mounted on said a pole, and having a concave surface on one side and a convex surface on the other side.

DESCRIPTION OF THE PREFERRED EMBODIMENTS

Figure 1:
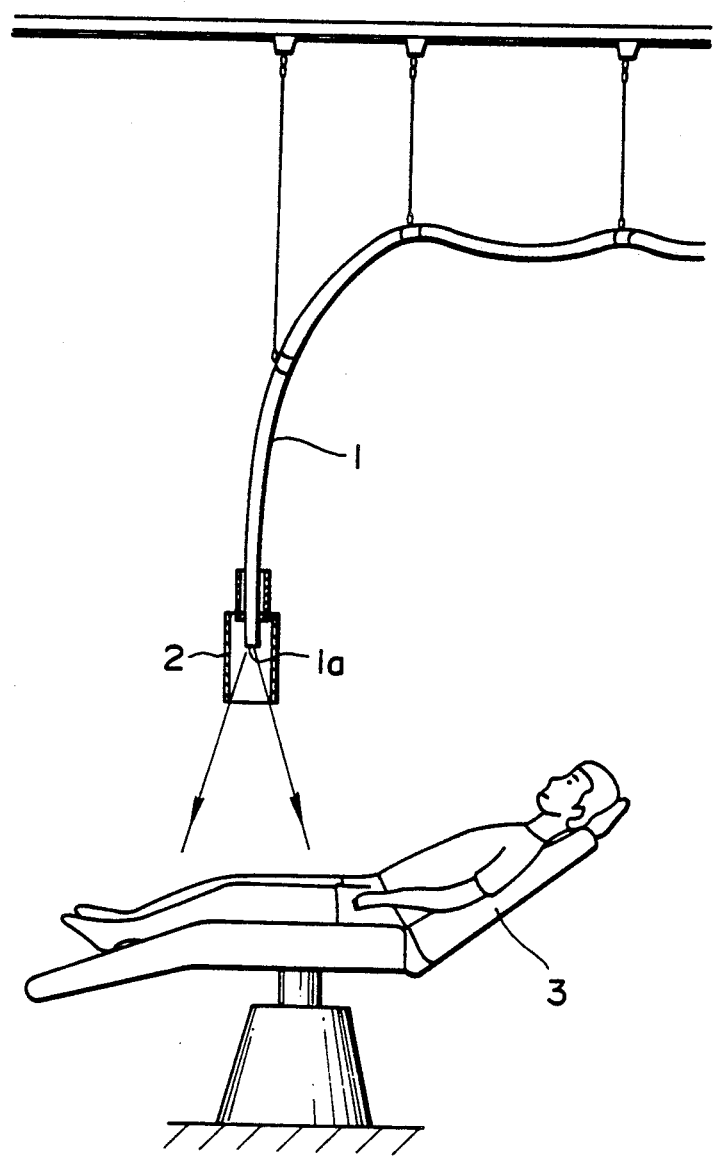
FIG. 1 is a construction view for explaining an example of a conventional light radiation device.

FIG. 1 is a construction view for explaining an example of the light radiation device for use in medical treatment as previously proposed by the present applicant. In FIG. 1, numeral 1 designates a fiber optic cable for receiving sunlight or artificial light at its input end, not shown in FIG. 1, and for transmitting the same therethrough. The light to be transmitted through said fiber optic cable 1 is one that corresponds to visible-spectrum light (white-colored light) obtainable in various ways as was previously proposed by the present applicant. In FIG. 1, numeral 2 designates a hood member installed at the light-emitting end portion 1a of said fiber optic cable and numeral 3 designates a chair for a patient. At the time of giving medical treatment, a patient is placed in the chair 3 and the visible-spectrum light thus transmitted through the fiber optic cable 1 is radiated onto the diseased part of the patient.

As mentioned above, the light to be radiated onto the diseased part of the patient is the one that corresponds to the visible-spectrum components of the sunlight and is free from harmful elements such as ultraviolet and infrared rays. Consequently, it may be possible to give medical treatments safely without fear of exposing a patient to harmful ultraviolet and infrared rays. However, the above-mentioned light radiation device has some drawbacks such as it is too large and too expensive to be used in a family setting.

In view of the foregoing, the present applicant has previously proposed a light radiation stand which is suitable for home use for radiating the light transmitted through a fiber optic cable.

Figure 2:
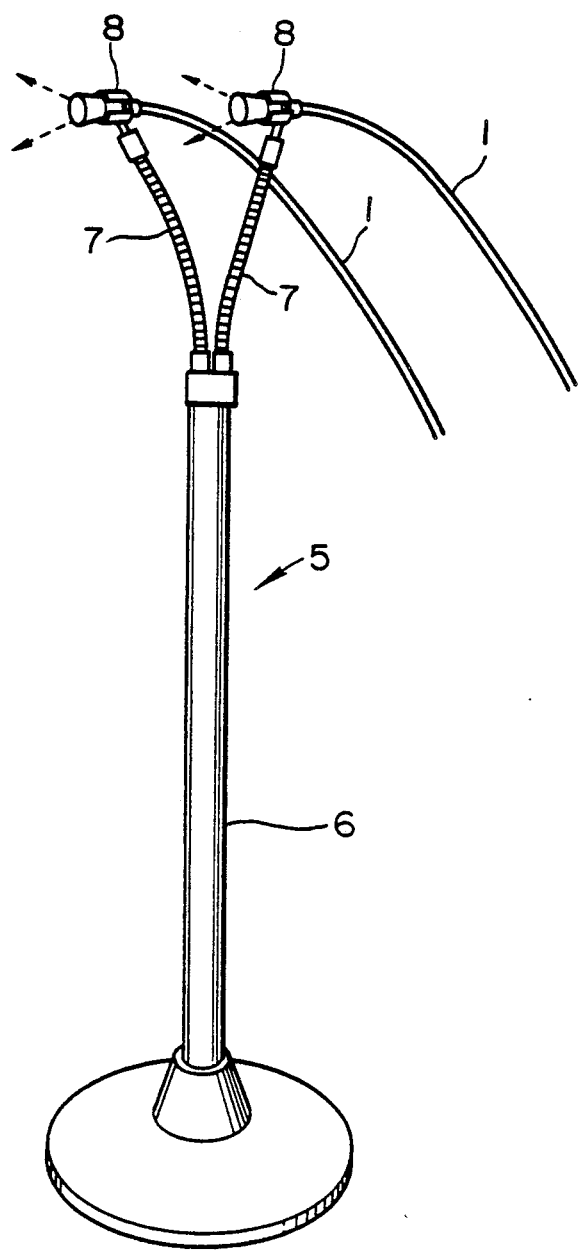
FIG. 2 is a view showing, by way of example, a light radiation device previously proposed by the present applicant.

FIG. 2 is a perspective view for explaining an example of a light radiation stand previously proposed by the present applicant. In FIG. 2, numeral 1 designates a fiber optic cable for transmitting solar rays collected by a solar ray collecting device not shown in FIG. 2 and numeral 5 designates a light radiation stand. Said stand comprises a stand base 6, one or more deformable flexible conduits 7 vertically installed at the stand base 6, a holding means 8 secured at the top of each conduit 7 so as to removably hold the cable 1. The light-emitting end of the cable is usually supported by the holding means while light radiation is being conducted. When the cable 1 is used while being supported by the stand, its light-emitting end can easily be directed in any desired direction by bending the conduit 7 since said conduit 7 can be freely bent and kept in that state. When the stand is not used for a long period, it can be stored in any desired place with a small area since the cable 1 can be removed from it.

As mentioned above, irradiating the skin's surface with light rays transmitted through a fiber optic cable can promote the health of persons and prevent people's skin from aging by increasing the body's life-sustaining activity.

Furthermore, it can aid in healing various kinds of diseases and scars and also aid in relieving the pain from such diseases. However, in the case of radiating the light rays, in particular, onto the face or other parts of the body that one cannot see oneself, one always feels anxious about the result of the radiation owing to the impossibility of checking how and where the light rays are falling. To solve this problem a hand mirror was adopted but it was found to be of no practical use and to be rather inconvenient because a patient could not hold a hand mirror for a long time and a suitable hand mirror was not always kept at hand.

In view of the foregoing description, the present invention was made in order to provide a light radiation stand having a pole being removable together with mirrors that are integrally mounted thereon.

Figure 3:
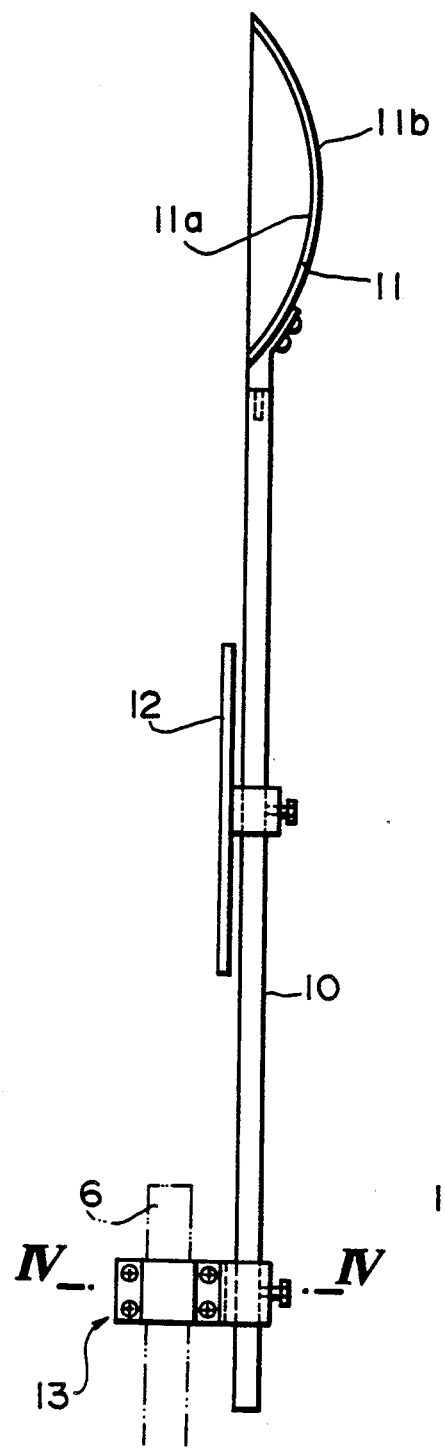
FIG. 3 is a basic construction view for explaining an embodiment of the light radiation stand according to the present invention.
Figure 4:
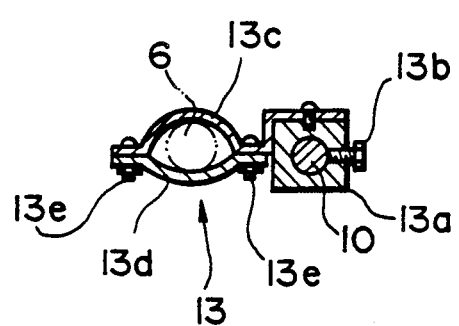
FIG. 4 is a cross-sectional view taken on line IV—IV of FIG. 3.

FIG. 3 is a basic construction view for explaining an embodiment of a light radiation stand according to the present invention. FIG. 4 is a cross-sectional view taken on line IV—IV of FIG. 3. In FIGS. 3 and 4, numeral 10 is a pole and 11 is a mirror rotatably mounted on said pole, said mirror having a convex surface 11a on one side and a concave surface 11b on the other side. 12 is a plane mirror rotatably mounted on the middle portion of the pole 10, 13 is a fixture for fixing the pole 10 to a support 6 shown in FIG. 2. Said fixture 13 consists of a block 13a having a hole for inserting the pole 10 therethrough, a setscrew 13b for securing the pole 10 in a given position and a pair of fitting elements 13c and 13d for fixing said block to the support 6. The fitting element 13c is secured at one end to the block 13a and has an arcuate half for clamping the support 6 while the fitting element 13d is of an arcuate half to be fixed to the arcuate half of the fitting element 13c. The block 13a is firmly secured to the support 6 by clamping the support 6 in these arcuate halves, for instance, with use of bolts and nuts 13e. In practice, after the fixture 13 is secured to the support 6, the pole 10 is inserted in the hole of the block 13a and is adjusted lengthwise so as to place the mirror in a desired position. Then the pole is clamped by tightening setscrews 13b. Normally, the radiation of the light rays from the light-emitting end of the fiber optic cable 1 can be carried out with a check of the place being radiated on the body with the help of a mirror 12. Furthermore, it is also possible to observe a locally enlarged virtual image of the object in a convex mirror 11b or to observe a wider virtual image of the object in a convex mirror 11a. While in FIG. 3 the mirror pole is fixed at the support 6 by using the clamping fixture 13, it will be easily understood that any fixture other than that shown in FIG. 3 may be applied and it may also be secured to the upper end of the support 6.

As is apparent from the foregoing description, according to the present invention, it becomes possible to easily attach mirrors to any existing light radiation stand and, furthermore, to easily select any suitable one of the mirrors provided depending upon the conditions for the radiation and therefore to get the best radiation possible on any portion of one's body without changing one's posture.

Figure 5:
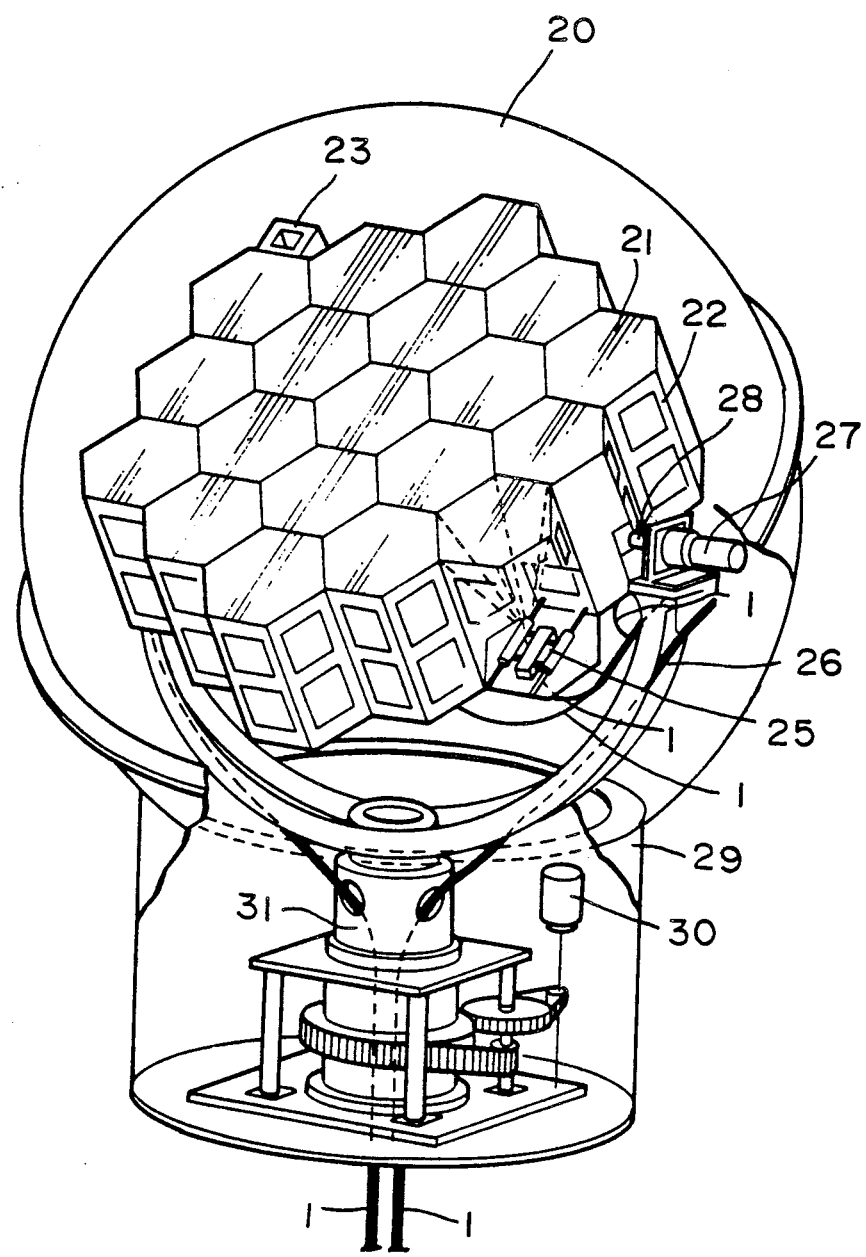
FIG. 5 is a view showing an embodiment of a solar ray collecting device used in the present invention.

FIG. 5 is a construction view for illustrating, by way of example, a solar ray collecting device for guiding the sunlight into the aforesaid fiber optic cable. In FIG. 5, numeral 20 is a transparent capsule, 21 is a Fresnel lens, 22 is a lens holder, 23 is a solar position sensor, 1 is a light guide or a fiber optic cable consisting of a large number of optical fibers with light-receiving end surfaces set on the focal plane of the Fresnel lens system, 25 is a holder of optical fibers, 26 is an arm, 27 is a pulse motor, 28 is a horizontal rotary shaft to be driven by the pulse motor 27, 29 is a base for supporting the protective capsule 20, 30 is a pulse motor and 31 is a vertical, rotary shaft to be driven by the pulse motor 30.

The direction of the sun is detected by means of a solar position sensor 23 and its detection signal controls the pulse motors 27 and 30 of the horizontal and vertical rotating shafts 28 and 31 respectively so as to always direct the solar position sensor toward the sun, and the sunlight focused by the lens 21 is guided into the light guide 1 through its end-surface set at the focal point of the lens. All of the light guides 1, separately placed at each lens, are bundled together in a fiber optic cable, the free end of which is led to any place where light radiation is needed for the afore-mentioned purposes.

Figure 6:
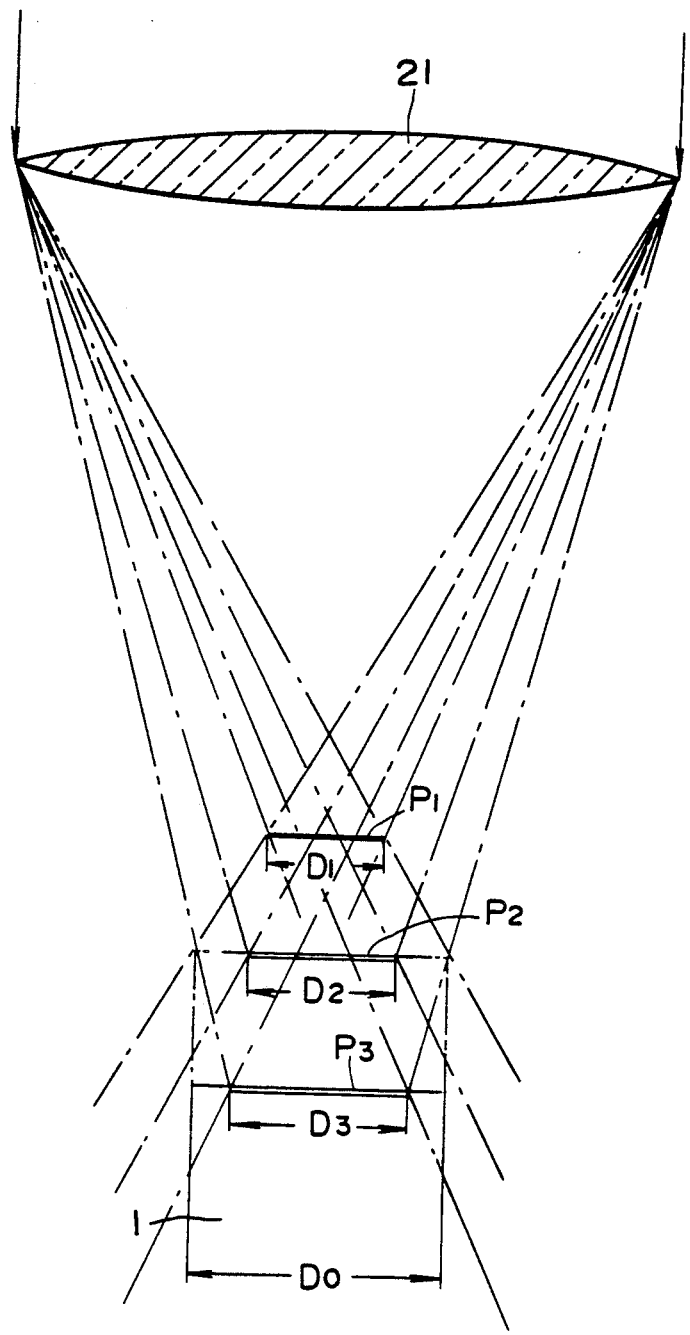
FIG. 6 is a view for explaining how to introduce visible-spectral solar rays into a light guide through the lens system of the solar ray collecting device.

FIG. 6 is a view for explaining how to guide the solar rays collected by the above-mentioned lens 31 into the light guides. In FIG. 6, 1 is a Fresnel lens or the like and 1 is a light guide which receives the sunlight focused by the lens 21 and which transmits the same to any desired place. In the case of focusing the sunlight through the lens system, the solar image has a central portion, consisting of almost white light and a circumferential portion containing therein a large amount of light components having wave-lengths corresponding to the focal point of the lens system. Namely, in the case of focusing sunlight through the lens system, the focal point and the size of the solar image will vary in accordance with the component wave-lengths of the light. For instance, the blue color light having a short wave-length makes a solar image of diameter D1 at position P1. Furthermore, the green color light makes a solar image of diameter D2 at position P2 and the red color light makes a solar image of diameter D3 at position P3. Consequently, as shown in FIG. 6, when the light-receiving end-surfaces of the light guides are set at position P1, it is possible to collect the sunlight containing plenty of the blue color components at the circumferential portion thereof. When the light-receiving end-surfaces of the light guides are set at position P2, it is possible to collect the sunlight containing plenty of the green color components at the circumferential portion thereof. When the light-receiving end-surfaces of the light guides are set at position P3 it is possible to collect the sunlight containing plenty of the red color components at the circumferential portion thereof. In each case, the diameter of the light guide 1 can be selected in accordance with the light components to be collected. For instance, the required diameters of the fiber optic cables are D1, D2 and D3, respectively, depending on the colors of the light rays to be stressed, i.e. the blue, green and red colors. In such a way, the required amount of the light guides can be saved and thereby the sunlight containing therein plenty of desired color components can be collected most effectively.

And further, as shown in FIG. 6, if the diameter of the light-receiving end-surface of the light guide is enlarged to D0, it may be possible to collect visible light containing therein all of its wavelength components. The light guides 1 may be pre-set at the focal point of the lens system in the manufacturing process or they may be left in an adjustable condition in the axial direction of the lens system to allow the user to adjust and fix said light guides depending upon the desired color of the light to be obtained. By selecting the wave-length of the light components to be introduced into the fiber optic cable, it becomes possible to use the light radiating system more effectively for various purposes. The above-mentioned example relates to the device for introducing the solar rays into the fiber optic cable. However, it is also possible to introduce artificial light into the fiber optic cable.

What is claimed is:

1. A light radiation stand comprising a stand base, holding means mounted on said stand base, fiber optic cable means for transmitting solar rays, said holding means holding said cable means on said stand base such that light rays emitted from said cable means are directed in a desired direction, an elongated pole, mounting means removably mounting said pole on said stand base, said elongated pole having a longitudinal axis and an outer end, first mirror means rotatably mounted on said outer end of said pole for rotation about a rotary axis coincident with said longitudinal axis of said pole, said first mirror means having two sides, one of said sides being a concave mirror surface, the other of said sides being a convex mirror surface, a second mirror means, and support means supporting said second mirror means on said pole between said outer end of said pole and said mounting means, said second mirror means being mounted on said pole for rotation about said longitudinal axis.

* * * * *